(12) United States Patent
Belhumeur et al.

(10) Patent No.: US 7,851,178 B1
(45) Date of Patent: Dec. 14, 2010

(54) BIOLOGICAL INDICATORS FOR VALIDATING A PRION STERILIZATION-PROCESS

(75) Inventors: Pierre Belhumeur, Laval (CA); Karine Julien, Montréal (CA); Maryam Tabrizian, Longueuil (CA); L'Hocine Yahia, Pointe-Claire (CA); Richard Marchand, Montréal (CA)

(73) Assignees: Polyvalor s.e.c., Montreal. Quebec (CA); Valorisation-Recherche, Montreal, Quebec (CA)

( * ) Notice: Subject to any disclaimer, the term of this patent is extended or adjusted under 35 U.S.C. 154(b) by 0 days.

(21) Appl. No.: 09/980,649

(22) PCT Filed: Apr. 20, 2000

(86) PCT No.: PCT/CA00/00446

§ 371 (c)(1),
(2), (4) Date: Jun. 4, 2002

(87) PCT Pub. No.: WO00/65344

PCT Pub. Date: Nov. 2, 2000

(51) Int. Cl.
*A61L 2/00* (2006.01)
*A61L 2/28* (2006.01)
*C12Q 1/22* (2006.01)

(52) U.S. Cl. .............. 435/31; 422/26; 422/119
(58) Field of Classification Search ............ 435/31; 422/26, 119
See application file for complete search history.

(56) References Cited

U.S. PATENT DOCUMENTS 5,357,636 A * 10/1994 Dresdner et al. ............. 2/161.7
5,633,349 A * 5/1997 Reichl ......................... 530/364

OTHER PUBLICATIONS

Safar et al. Thermal stability and conformational transitions of scrapie amyloid (prion) protein correlate with infectivity. 1993, Protein Science 2:2206-2216.*
Feldman et al. Compatibility of Medical Devices and Materials with Low-Temperature Hydrogen Peroxide Gas Plasma. 1997. http://www.epotek.com/SSCDocs/whitepapers/Tech%20Paper%2059.pdf.*
Prusiner. Prions. 1998. PNAS 95:13363-13383.*
Parkin et al. Amyloid precursor protein, although partially detergent-insoluble in mouse cerebral cortex, behaves as an atypical lipid raft protein. Biochem. J. 1999 344:23-30.*
DeArmond. Alzheimer's disease and Creutzfeldt-Jakob disease: overlap of pathogenic mechanisms. Curr. Opin. Neurol. 1993, Abstract.*
Wickner. 1994. [URE3] as an Altered URE2 Protein: Evidence for a prion analog in *Saccharomyces cerevisiae*. Science. 264:566-569.*
Coustou et al. 1997. The protein product of the het-s-heterokaryon incompatibility gene of the fungus *Podospora anserina* behaves as a prion analog. PNAS 94:9773-9778.*
Taylor et al. 1999. Prion Domain Initiation of Amyloid Formation in Vitro from Native Ure2p. Science. 283:1339-1343.*
Glover. J.R., Kowal, A.S., et al. Cell (1997) 89:811-819.
Hill, A.F., Antoniou, M. and Collinge, J., Journal of General Virology (1999) 80:11-14.
Jarvis, W.R. Hospital Infection Control (1985) 12 (12):145-148.
King, C., Tittmann, P. et al. Proc. Natl. Acad. Sci. USA (1997) 94:6618-6622).
Rosenberg, R.N. et al., Annals of Neurology (1986) 19(1):75-77.
Sambrook, J., Fritsch, E.F.; and Maniatis, T. Molecular Cloning, a laboratory manual. Cold Spring Harbor Laboratory Press, 2nd edition, 1989.
Tuite MF and Lindquist SL , TIG (1996) 12 (11): 467-471.
Wickner, RB. PNAS (1997) 94 : 10012 to 10014.
Dental Products Report, Oct. 1995, pp. 96-104.

* cited by examiner

*Primary Examiner*—Taeyoon Kim
(74) *Attorney, Agent, or Firm*—Klauber & Jackson, LLC

(57) ABSTRACT

The present invention relates to a method of evaluating the efficiency of sterilization processes by measurement of degradation level of prion protein indicators. When exposed to sterilization conditions, prion indicators are degraded in a manner to proportionally indicate the level of degradation of prion proteins themselves on medical devices or other surfaces usable in surgery and health cares.

13 Claims, 5 Drawing Sheets

Coomassie blue staining     α-6XHIS

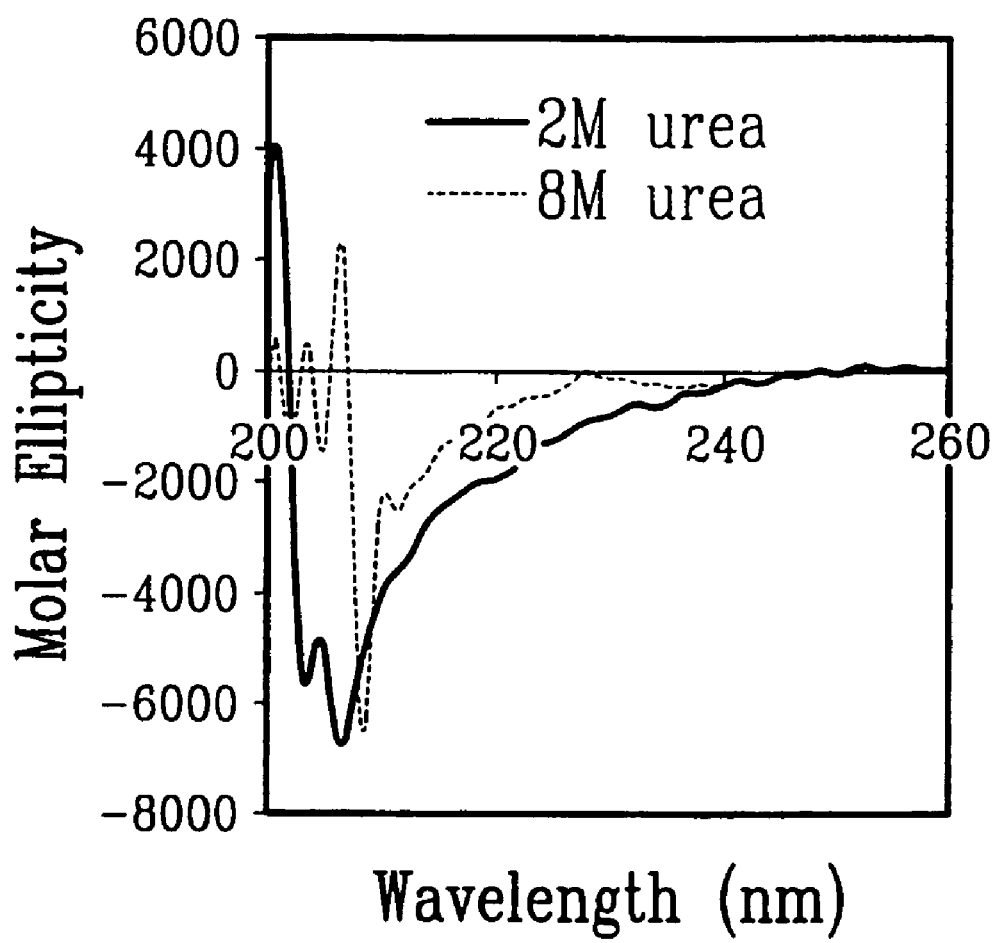

Coomassie blue
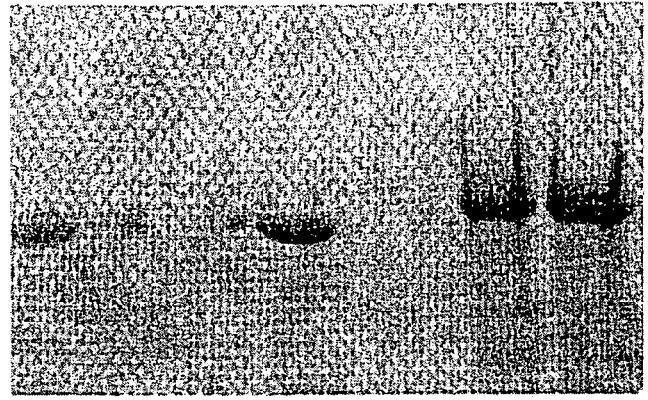
FIG. 5A
α-6XHIS
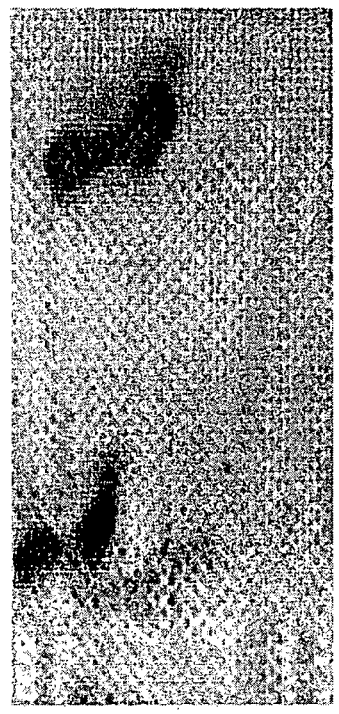
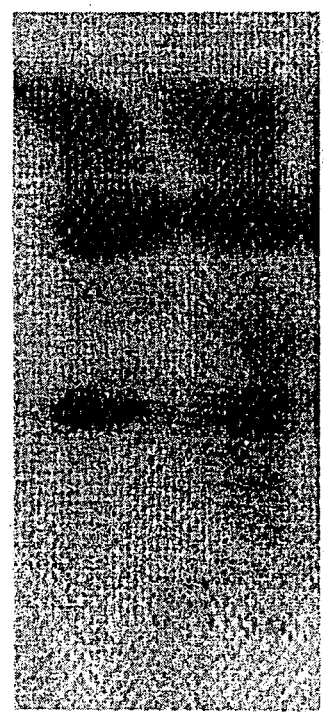
FIG. 5B

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
agtggatcct cggattcaaa ccaaggcaa                              29

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
cgcgtcgaca tcgttaacac ctccgtc                                27
```

BIOLOGICAL INDICATORS FOR VALIDATING A PRION STERILIZATION-PROCESS

BACKGROUND OF THE INVENTION (a) Field of the Invention

The invention relates to a method of control of sterilization process, which comprises the steps of measuring the level of degradation of a prion protein degradation indicator when exposed to different sterilization processes.

(b) Description of Prior Art

Biological indicators are considered essential to evaluate the efficacy of any sterilization procedure since chemical and physical monitors are not completely reliable. The latter are useful for detecting gross sterilization, but spore tests are absolutely required for any assurance of sterilization since they are more resistant to heat than viruses and vegetative bacteria. The biological indicators are usually composed of bacterial spores of *Bacillus stearothermophilus* (for autoclaves and chemical vapor sterilizers) or *Bacillus subtilis* (for dry heat and ethylene oxide sterilizers) which are removed after sterilization treatment and incubated at the appropriate temperature to observe any microbial growth (Dental Products Report, October 1995, pp. 96-104). However, in this day and age, bacterial spores are no longer the most resistant life forms since the discovery of prions.

Sup35 protein (hereby referred to as Sup35p) carrying [PSI+] is a prion-like protein due to its striking similarities to prions. Indeed, the N-terminal of Sup35p is insoluble in non-ionic detergents and partly resistant to proteases' action. In addition, it principally forms abnormal amyloid filaments composed mainly of β-sheets, as opposed to the normal isoform of the protein mostly formed of α-helices (Glover. J. R., Kowal, A. S., Et al. *Cell* (1997) 89:811-819; King, C., Tittmann, P. et al. *Proc. Natl. Acad. Sci. USA* (1997) 94:6618-6622).

The intracellular accumulation of these abnormal prion filaments is responsible for inducing transmissible spongiform encephalopathies in both animals and humans, hence the importance of degrading the filaments in order to prevent any iatrogenic transmission of the disease. Several cases of iatrogenic contamination have been reported due to the utilization of contaminated medical equipment, such as EEG electrodes, which had been previously in contact with Creutzfeld-Jakob patients and inadequately sterilized (Jarvis, W. R. *Hospital Infection Control* (1985) 12 (12):145-148). Since there also remains the possibility of blood contamination, which has not yet been ruled out, most medical instruments enter in the category of being at risk of being contaminated but that, at different levels depending on the case history of the patient.

The unavailability of sterilization indicators to attest of prion degradation renders the devices inadequate and even dangerous for multiple usage. As of today, most countries have adopted similar requirements for sterilization of contaminated instruments. The recommended procedures for sterilization of medical instruments used on patients at high risk is the incineration of any disposable equipment that has been in contact with a patient or, at the very least, soaking in 1N sodium hydroxide, which is very corrosive for metallic instruments, or autoclaving at 132° C./1 atm pressure for an hour (Rosenberg, R. N. et al., *Annals of Neurology* (1986) 19(1):75-77; Galtier, F., *J. Pharm. Clin.* (1994) 13:317-9) which can deform thermosensitive materials such as polymers.

It would be highly desirable to be provided with a novel indicator of prion degradation and therefore, of complete sterilization of medical devices.

SUMMARY OF THE INVENTION

The solution therefore lies in the development of this novel sterilization indicator, based on Sup35 protein, which would insure that all the medical devices are thoroughly sterilized and fit for utilization by proving the degradation of prions. This indicator could be used for any sterilization process commonly used, as well as novel techniques such as low-temperature plasma gas or ozone-based sterilizers for instance.

One aim of the present invention is to provide a novel indicator of prion degradation and therefore, of complete sterilization of medical devices.

In accordance with the present invention there is provided a method of evaluating the efficiency of a sterilization process, which comprises the steps of:

a) subjecting a sufficient amount of at least one prion protein degradation indicator in a container to the sterilization process; and b) determining the level of degradation of the indicator.

An aspect of the invention is that the indicator may be transcribed by a gene naturally occurring in a fungus, most particularly in *Saccharomyces cerevisiae*, or *Podospora anserina*.

The indicator may be transcribed by gene selected from the group consisting of SUP35, URE2, and HET-s.

The indicator may be selected from the group consisting of Sup35p, Ure2p, Het-s protein, and combination thereof.

The indicator may be a purified form naturally occurring in fungi, a recombinant form, an analog, a mutant, or a fragment of the indicator.

The indicator may be a biological indicator, biochemical indicator, or chemical indicator.

Of particular aspects of the invention, the measurement of indicator degradation may be performed by determining the weight or the mass, quantifying radicals, colorimetric variations, radiometry, nephelometry, immuno-enzymatic method, Western blotting, dot blotting, radioimmuno assay, circular dichroism, electron microscopy, fluorescent microscopy, FTIR, Congo red binding, or proteinase digestion.

The sterilization process may be performed by autoclaving, chemical exposure, dry heating, low temperature plasma gas, ozone-based exposure, or sterilization techniques using alkylant and/or oxidizing sterilizing agents.

The chemical exposure may be a vapor or a solution selected from the group consisting of detergent, ethylene oxide, protease, sodium hydroxide, and enzyme.

The amount of indicator exposed to sterilization processes may be between 0.1 ng to 100 g.

The container may be of a material selected from the group consisting of paper, glass, borosilicate, metal, polymer, alloy and composite.

The container may also be porous, permeable, or semi-permeable.

BRIEF DESCRIPTION OF THE DRAWINGS

FIG. 3 illustrates circular dichroism analysis of Sup35 N-terminal protein;

FIG. 5 illustrates the effect of Sterrad® 100 treatment on Sup35 N-segment integrity.

DETAILED DESCRIPTION OF THE INVENTION

Figure 1A:
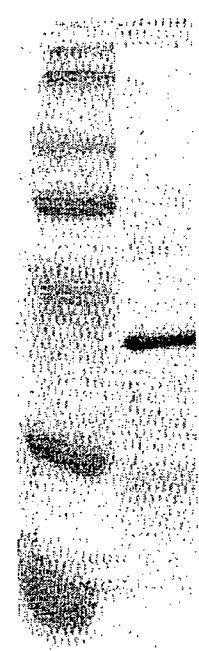
FIG. 1 illustrates the production of bacterially-expressed recombinant SUP35 N-terminal segment.

In accordance with one embodiment of the present invention, there is provided a novel indicator of prion degradation and therefore, of complete sterilization of medical devices.

A particular aspect of the present invention is the use of [PSI+], a non-mendelian genetic factor encoded by the SUP35 gene of the budding yeast *Saccharomyces cerevisiae*, and Het-s encoded by *Podospora anserina*, as indicator of prions protein degradation in sterilization of medical devices and all other apparatus, surfaces, or thinks used in surgical procedures and health cares.

Another embodiment of the invention is the use of fertilisation indicators formed of Sup35p, Ure2p, Het-s, or Psi that is quite simple to use. The indicator may be in solution within a glass vial, so that the container would be resistant to any sterilization technique, whether it is autoclaved using high heat and pressure or low-temperature techniques such as plasma. Non-denaturing buffers such as Tris/EDTA, TFA/acetonitrile, or even 2M urea would be used in order to maintain the integrity of the Sup35p filaments.

It is known that a single infectious unit of prion corresponds to $10^4$-$10^5$ PrP molecules, or 0.5-5 fg, which is below the detection limit of SDS-PAGE gels (Hill, A. F., Antoniou, M. and Collinge, J., *Journal of General Virology* (1999) 80:11-14).

Hence, in an other embodiment of the invention, there is a proof of degradation of a larger amount of protein, such as 10 μg, that insure that complete sterilization has occurred and therefore, that the medical instrument is safe for reuse. This is based on the consideration that if there is a structural modification of the protein, i.e. if the protein undergoes a change in conformation or degradation following exposure to the various sterilization techniques, it is rendered inactive and therefore, non-infectious.

Moreover, by using 10 μg of indicator, the invention allows to be able to easily detect any degradation of the protein by SDS-PAGE gels stained with Coomassie Brilliant Blue for example, a common laboratory technique, since as little as 0.1 μg of protein can be detected by this method (Sambrook, J., Fritsch, E. F., and Maniatis, T. Molecular Cloning, a laboratory manual. Cold Spring Harbor Laboratory Press, $2^{nd}$ edition, 1989).

In an other embodiment of the invention, degradation or alteration can also be estimated by Western Blot or dot blot using an antibody against the tagged protein to estimate the lack of or a modified detection signal being generated by any alteration of the target Sup35 protein. In addition, the indicator degradation could also be detected by color change of the solution, which would confirm sterilization. If needed, techniques such as circular dichroism, electron microscopy, fluorescent microscopy, FTIR, Congo Red binding or proteinase K digestion could also be used to detect the change in conformation of the sterilized protein from β-sheets to α-helices, thus displaying the degradation of the protein, and therefore, its inactivation.

Since the materials used for the indicator (glass vials, solutions, etc.) are quite common and inexpensive, the total cost of production of such an indicator is reasonably low. It therefore renders it very affordable for any institution, hospital or industry that would purchase it to ensure the safety of their medical instruments.

In an embodiment the invention, the sterilization indicator is also cost effective since all instruments can be tested and may be proven safe for reuse, if and only if the sterilization indicator demonstrate complete inactivation following an entire cycle of sterilization. Common spore tests do not rule out completely the possibility that active residual proteins do remain on the surface of the devices. Moreover, these techniques can alter the quality of the instruments, hence the quality of the medical care provided. Replacing all hypothetically contaminated instruments would indeed be very costly for medical services and reusable instruments might be discarded in the process for fear of contamination.

MATERIALS AND METHODS

Bacterial Strains

For cloning experiments, the *Escherichia coli* SURE strain was routinely used (InVitrogen™). For protein expression and purification, expression plasmid was transformed into the *E. coli* BL21(pRep4) strain (Novagen).

DNA Manipulations and Protein Purification

Standard DNA techniques have been described before (Sambrook et al., 1989). DNA sequencing was performed at Institut Armand Frappier DNA sequencing facilities (Montreal, Canada). Protein expression/purification procedures were performed as described by the manufacturer (Clontech).

Cloning of the Aggregating N-Terminal Domain of Sup35 in a Bacterial Expression Vector The first 759 bp region of Sup35 encoding the peptidic region sufficient for aggregation was PCR amplified from a genomic clone in pEMBLyex4 kindly provided by Dr. Ter-Avanesyan (Moscow, Russia; Glover. J. R., Kowal, A. S., et al. *Cell* (1997) 89: 811-819). The following primers were used: (a) 5'-AGTGGATCCTCGGATTCAAACCAAGGCAA-3' (SEQ ID NO: 1) (introducing a BamHI restriction enzyme site, underlined), and (b) 5'CGCGTCGACATCGTTAA-CACCTCCGTC-3' (SEQ ID NO: 2) (introducing a SalI restriction enzyme site, underlined). The fragment was then cloned into pT7Blue3 (Perfectly Blunt Cloning Kit-Novagen) into the SURE *E. coli* strain (InVitrogen). Positive clones were sequenced to assess any mutation or deletion in the gene. The Sup35 gene N-segment was then excised with BamHI and SalI and inserted into the expression vector pQE30 (Qiagen) using the same restriction sites. Positive clones in pQE30 were the transferred in BL21 [pREP4] for protein expression and purification.

Protein Expression and Purification

Protocols were performed mostly according to the manufacturers. Induction of a 1 L of bacterial culture ($OD_{600}$ of 0.8) was done using IPTG (final concentration of 1 mM) for an hour at room temperature. The cells were harvested, resuspended in 50 ml of Buffer B (8M urea, 0.1M Na-phosphate, 0.01M Tris HCl pH 8.0), sonicated and centrifuged at 10 000 xg for 15 min at 4° C. The supernatant was collected and loaded onto a $Ni^{2+}$-NTA column (TALON metal affinity resin; Clontech) for affinity chromatography using a pH gradient with the denaturing 8M urea purification protocol from Qiagen. The samples were analyzed by SDS-PAGE (gel electrophoresis technique used to estimate the size and amount of the protein) and by Western Blot using a mouse anti-histidine antibody (Qiagen) against the 6-histidine tail present in the pQE30 vector, in order to specifically detect the protein. After separation of the proteins on SDS-PAGE and electroblotting onto nitrocellulose, the membrane was incubated with the primary antibody (anti-HIS RGS, from Qiagen, 1:2000) in 10 mM Tris pH 7.5, 100 mM NaCl (TBS) with 5% Non fat milk, 0.1% Tween™20 for an hour. There was then 3 washes (10 5 minutes each) with TBS 0.1% Tween™20. Detection was performed with the BM Chemiluminescence Kit using an anti-mouse antibody coupled to horseradish peroxydase (1:4000) (Roche Diagnostics). Membranes were finally exposed onto radiographic films and developed.

Filament Induction and Analysis

To induce the formation of the filaments, a 6 h to 12 h dialysis at room temperature of the protein (9 µM, in 8M urea solution) against either a 0.2M urea, 30 mM Tris-HCl pH 8.0, 300 mM NaCl (referred to as "2M urea") solution or 0.1% Trifluoroacetic acid, 40% acetonitrile solution (referred to as "TA") or a Tris/EDTA solution (10 mM Tris pH 8, 0 EDTA 1 mM, "TE") was performed.

Transmission Electron Microscopy (TEM)

Samples (50 µl) of the filament suspension were sedimented by ultracentrifugation (178000 g, 20 min, Beckman Airfuge) onto a carbon-formvar coated copper grids (3 mm diameter, 200 mesh). These grids were then negatively stained by 3% (wt/vol) PTA (Phosphotingstic acid) and by 2% (wt/vol) uranyl acetate for 1 minute each. The samples were then observed using a Transmission Electron Microscope Hitachi H-7100 at 75 kV.

Circular Dichroism (CD) Spectroscopy

CD spectra of a 9 µM filament suspension (2M urea) were recorded on a Jasco J710 Spectropolarimeter at room temperature using a 0.05 cm pathlength cell. Samples were scanned with the following settings: scan speed: 100 nm/min; response time: 0.25 sec; accumulations: 3 (empty cell), 5 (buffer alone) and 10 (protein samples); sensitivity: 50 mdeg; starting wavelength: 260 nm; ending wavelength: 200 nm.

Sterilization Assays

Autoclaving at 121° C. for an hour and Sterivac® (ethylene oxide) was used as negative controls; Sterrad® 100, which uses a combination of hydrogen peroxide and gas plasma as sterilizing agents were used as the experimental processes. The samples were submitted to either one entire cycle of each process or to only a quarter of a cycle, as it was the case with ozone. Following this, the degradation of Sup35 was evaluated. 10 µg of protein was exposed to the sterilization processes described in Table 1. Degradation of the protein was assayed by SDS-PAGE using. Silver Nitrate and Coomassie Blue coloration as well as TEM micrographs (filament formation). Immunological detection using chemiluminescence (described above) was also used, following the sterilization processes.

TABLE 1

Sterilization cycles used for the evaluation of the degradation of Sup35p

| Sterilization process | Sterilizing agent | Cycle | Time required for complete cycle |
|---|---|---|---|
| Autoclave | Heat | Temperature: 121° C. Pressure: 1 atm | 1 hour |
| Sterivac ®, 3M | Ethylene Oxide (EO) | (a) Temperature: 134° F. (b) Preheating time: 30 min. (c) Sterilization time: 2 h10 (d) Ventilation time: 12 h | Approx. 16 hours |
| Sterrad ® 100, Johnson and Johnson | $H_2O_2$ and gas plasma | (a) vacuum (0.3 torr): 5-20 min (b) injection of $H_2O_2$ 58% + $H_2O$: 6 min (c) diffusion (0.5 torr): 44 min (d) plasma: 15 min | Approx. 75-95 min. |

RESULTS

Purification and Characterization of SUP35 N-Protein

Figure 1B:
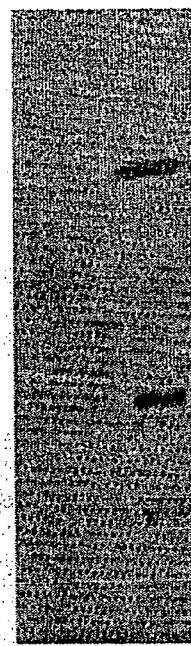
Figure 2A:
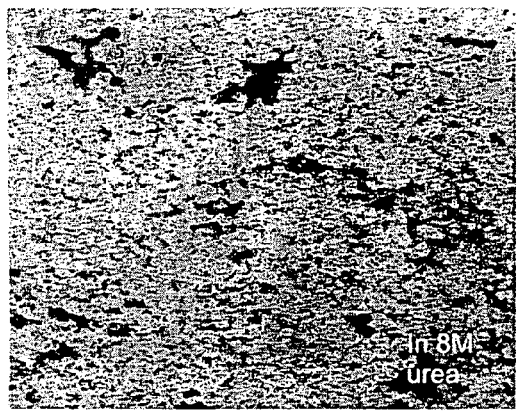
FIG. 2 illustrates the transmission electron microscopy of recombinant Sup35 N-terminal segment in different solutions.
Figure 2B:
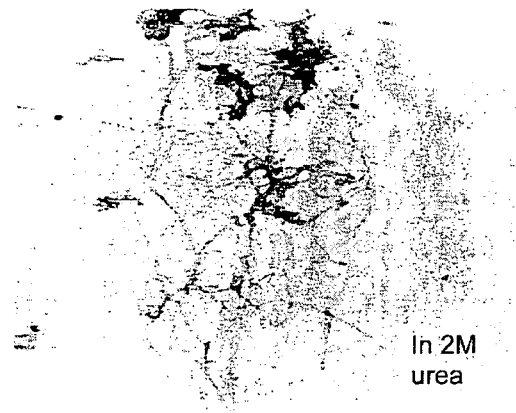
Figure 2C:
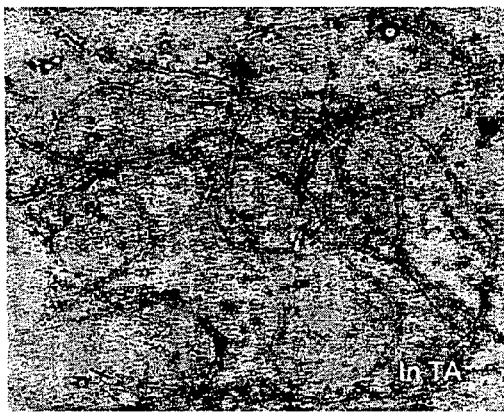
Figure 2D:
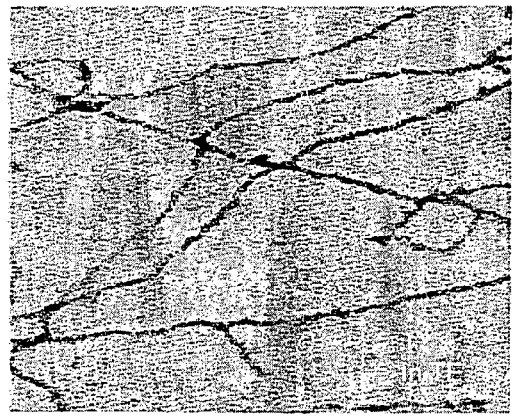

The SUP35 gene encodes a 76.5 kDa ribosome-associated protein. However, it has been shown that only the first 114 amino acids are sufficient for filament formation (King, C., Tittmann, P. et al. *Proc. Natl. Acad. Sci. USA* (1997) 94:6618-6622). DNA primers similar to those already described (Glover. J. R., Kowal, A. S., Et al. *Cell* (1997) 89:811-819) were used to amplify the first 639 nucleotides including and from the initiation codon, using a genomic clone provided by Dr. Ter-Avanesyan. Glover et al. (1997) has shown that the resulting 213 amino acid long peptide could exhibit many biochemical features similar to prions. The expressed protein, purified under denaturing conditions, has an apparent molecular weight of 30 kDa, as estimated by SDS-PAGE analysis (FIG. 1, left-hand panel). Bacterially-expressed protein from purified through nickel chromatography (Materials and Methods) and protein samples were analyzed by SDS-PAGE and Coomassie Blue staining (left-hand panel) and Western blotting with an antibody against the 6×HIS tag (right-hand panel). Identity of the protein observed by Coomassie staining of the gel was confirmed, using and antibody raised against the 6×HIS tag, which is present in the bacterially-expressed protein due to its incorporation in frame at the N-terminus of the peptide (FIG. 1, right-hand panel).

To ensure that the purified SUP35 N-protein was behaving similarly to prions, the ability to undergo ordered aggregation was investigated, forming amyloid-like filaments. Those can be observed by transmission electronic microscopy (TEM). TEM images of protein suspension in 8M urea or slowly dialyzed against 2M urea or trifluoroacetic acid/acetonitrile 0.1%/40% (TE) solution and maintained at 4° C. for a week are shown in FIG. 2. Bacterially-produced protein in 8M urea was dialyzed against either 2M urea, trifluoroacetic acid/acetonitrile 0.1%/40% (TA) or Tris-EDTA (TE), maintained for one week at 4° C. and processed for TEM. (M refers to the marker). Indeed, the Sup35 protein unless in 8M urea solution (even for weeks at 4° C.) tend to form aggregates easily observed by TEM analysis.

Moreover, extensive aging of the solutions containing Sup35p should exhibit β sheet-like characteristics, with a single differential absorption minimum near 220 nm when analyzed by circular dichroism. As it can be seen in FIG. 3, it is possible to distinguish a spreading of the peak of protein in 2M urea (ordered aggregates) from the random coiling of Sup35p in the 8M urea solution.

From these results, it is concluded that the bacterially-expressed N-portion of the Sup35 protein behaves as expected and exhibits many biochemical features resembling to prions.

Sup35p Stability to Various Sterilizing Process

The efficacy of sterilizing treatments was assessed based on their impact on the integrity of the Sup35p. Samples of the Sup35 protein, kept under different forms, were processed and then analyzed by SDS-PAGE and/or Western blotting.

Figure 4A:
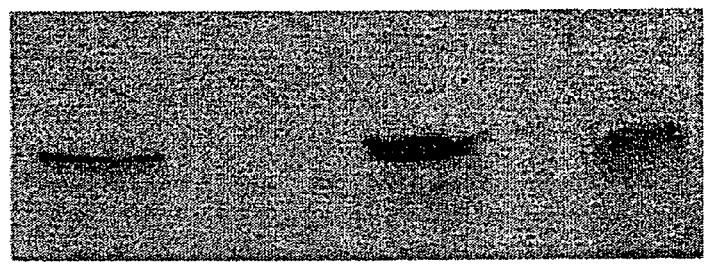
FIG. 4 illustrates the effect of autoclave and ethylene oxide treatments on Sup35 N-segment protein integrity.
Figure 4B:
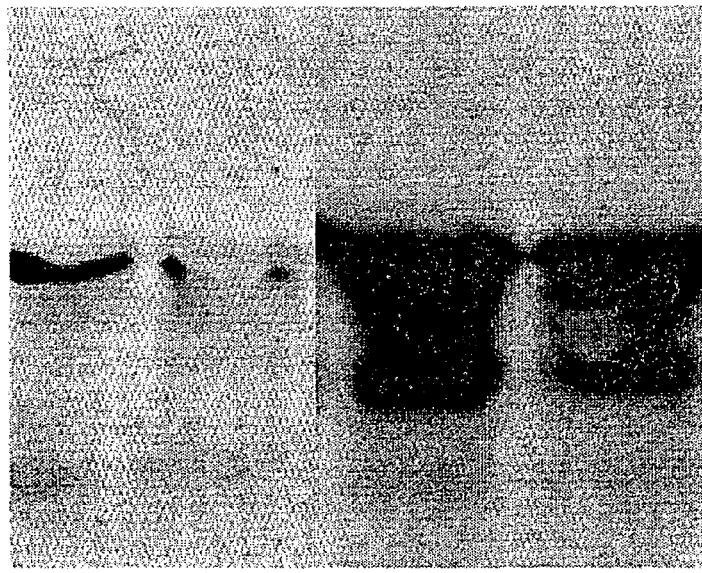

The Applicants are the first to confirm that classical autoclave sterilization cycle was unable to destroy Sup35 protein as it is the case for prions. No intact protein could be recovered from Sup35p kept in 8M urea (no aggregates) after autoclave while filaments from the Sup35 protein in TFA were resistant to degradation, as seen from Coomassie staining of the SDS-PAGE (FIG. 4, top panel, Sup35 protein in 8M urea or in TA was processed for sterilization and then analyzed for integrity by SDS-PAGE. (U refers to untreated and T, to treated samples)). Similar results were obtained when the same samples were exposed to ethylene oxide (FIG. 4, bottom panel). From these results, it is conclude that autoclave and ethylene oxide treatments are unable to degrade the orderly aggregated Sup35 protein.

On the other hand, the 8M urea and 2M urea proteins were degraded upon treatment to the Sterrad® 100 treatment (oxidative process, combining hydrogen peroxide and gas plasma). Aggregates of the 2M urea protein could be destroyed by this treatment. Aggregates of the TA protein could however resist to the sterilizing process, as evaluated by the intact protein seen in the Coomassie Blue stained gel (FIG. 5, top panel, Sup35 protein samples in 8M urea, 2M urea or trifluoroacetic acid/acetonitrile 0.1%/40% (TA) were processed and the remaining intact protein was analyzed by SDS-PAGE revealed by Coomassie Blue staining (top panel) or Western blot analysis, with an antibody against 6×HIS tag (bottom panel). (U refers to untreated, T to treated samples, and * in Western blot panel to intact Sup35p). To increase the sensitivity of the detection technique and to ensure that this treatment could indeed degrade the filaments of the 2M urea Sup35 protein, Western blot analysis was performed using an antibody detecting the 6×HIS tag present at the N-terminus of the bacterially-expressed protein (FIG. 5, bottom panel). These experiments show that the Sterrad® 100 process can degrade the aggregates of the 2M urea kept Sup35 protein.

The only resistance observed was in the samples of the Sup35 placed in TA. There are two possible explanations for these unexpected results. First, there could have been an interaction between the Trifluoroacetic acid/acetonitrile and the hydrogen peroxide used as the sterilizing agent in Sterrad systems, which could have inhibited the oxidative potential of this process. This increased resistance could also have been caused by the protonation of the protein by TA solution, which would render the protein less susceptible to oxidative effect of hydrogen peroxide. TEM analyses of samples in different solutions for sterilization procedures used in this study indicated desintegrity of Sup35 filament conformation. These observations confirmed the results obtained by other methods, such as Coomassie Blue and Western Blot as described here-above.

From these results, it is expected that other sterilization techniques which use oxidative sterilizing agents, such as ozone-, peracetic acid-based sterilizers, etc. would also be efficient to alter Sup35 protein.

While the invention has been described in convection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of evaluating the efficiency of a sterilization process on yeast prion proteins comprising:
    a) subjecting a sufficient amount of at least one prion protein degradation indicator in a container to said sterilization process such that degradation of prion proteins occurs; and
    b) determining the level of degradation of said prion protein degradation indicator, wherein said prion protein degradation indicator is transcribed by a gene selected from the group consisting of SUP35, URE2 and HET-s and is in amyloid form and wherein said level of degradation of said prion protein degradation indicator is indicative of the efficiency of said sterilization process.

2. A method of evaluating the efficiency of a sterilization process on yeast prion proteins, comprising:
   a) subjecting a sufficient amount of at least one prion protein degradation indicator in a container to said sterilization process such that degradation of the prion protein occurs, and
   b) determining the level of degradation of said prion protein degradation indicator, wherein said prion protein degradation indicator is selected from the group consisting of Sup35p, Ure2p, Het-s protein in amyloid form, and combination thereof and wherein said level of degradation of said prion protein degradation indicator is indicative of the efficiency of said sterilization process.

3. The method according to claim 1, wherein said indicator is a purified naturally occurring form, a recombinant form, a mutant, or a fragment thereof, wherein said indicator is insoluble in non-ionic detergents, resistant to proteases' action, and forms amyloid filaments composed of β-sheets.

4. The method according to claim 1, wherein step b) is performed by determining a weight or a mass, quantifying radicals, colorimetric variations, radiometry, nephelometry, immuno-enzymatic method, Western blotting, dot blotting, radioimmuno assay, circular dichroism, electron microscopy, fluorescent microscopy, Fourier transform infrared spectroscopy (FTIR), Congo red binding, or proteinase digestion.

5. The method according to claim 1, wherein said sterilization process is performed by autoclaving, chemical exposure, dry heating, low temperature plasma gas, ozone-based exposure, or sterilization techniques using alkylating and/or oxidizing sterilizing agents.

6. The method according to claim 1, wherein said chemical exposure is a vapor or a solution selected from the group consisting of detergent, ethylene oxide, protease, sodium hydroxide, and enzyme.

7. The method of claim 1, wherein said amount of indicator of step a) is between 0.1 ng to 100 g.

8. The method of claim 1, wherein said container is of a material selected from the group consisting of paper, glass, borosilicate, metal, polymer, alloy, and composite.

9. The method according to claim 1, wherein said container is porous, permeable, or semi-permeable.

10. The method of claim 3, wherein said indicator is a purified naturally occurring protein in amyloid form in *Saccharomyces cerevisiae* or *Podospora anserin*.

11. The method according to claim 3, wherein the fragment comprises:
   a. the first 759 nucleotides of SUP35 counted from the A of the initiation codon encoding the peptidic region,
   b. the region coding for amino acids 2-114 of Sup35p; or
   c. the first 639 nucleotides of SUP35 counted from the A of the initiation codon.

12. The method according to claim 1 wherein the sterilization process comprises ozone treatment.

13. The method according to claim 1 wherein the determining the level of degradation of said prion protein degradation indicator is performed by Western Blot analysis.

* * * * *